United States Patent [19]

Holtkamp

[11] Plant 4,547

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 15,822

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill

*Assistant Examiner*—James R. Feyrer

*Attorney, Agent, or Firm*—Donald D. Jeffery

[57] ABSTRACT

An African violet known by the cultivar name Alberta, having a vigorous growth habit; 12 or more strong flower stems each of which carries 12 or more violet-shaped flowers which are generally white with purple centers and edges, with the flowers normally containing five petals, with an occasional small petal appearing at the center attached to the receptacle; uniform bouquet and by its long blooming period.

1 Drawing Figure

The present invention comprises a new and distinct cultivar of African violet plant, botanically known as *Saintpaulia ionantha,* and hereinafter referred to by the cultivar name Alberta.

The new cultivar was referred to during the breeding and selection process by the designation C 44/1-98/79, and is a product of a planned breeding program. Alberta is generally characterized by generally violet-shaped flowers, strong flower stems, uniform bouquet, prolonged blooming with non-dropping flowers, and up to 12 and more flowers per stem. The flowers are generally white, with purple tinging on the edges and centers. These traits in combination were not present in previously available commercial cultivars.

The new cultivar was originated from a cross made in a controlled breeding program in Isselburg, Rhineland, Germany. The female, or seed parent was a cultivar designated Velli/Wifo blue, unpatented. The male, or pollen parent was a cultivar designated 86/75 white star, also unpatented.

The new cultivar Alberta was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction. The following observations, meausurements and values described plants grown in Isselburg, Rhineland, Germany, under greenhouse conditions which closely approximate those generally used in commercial practice.

The following traits have been repeatedly observed and are determined to be basic characteristics of Alberta, which in combination distinguish this African violet as a new and distinct cultivar:

(1) Upright and strong flower stems.

(2) Up to 12 or more violet-shaped flowers per stem.

(3) The base color of the flowers is white, with the center and edges being red-violet.

(4) Vigorous growth habit, producing 12 or more flower stems.

(5) Flexible leaves and petioles.

(6) Long blooming period.

(7) The petals are normally five in number, three large and two small, although occasionally an additional small petal will appear at the receptacle.

The accompanying photographic drawing shows a typical specimen plant of the new cultivar. The colors appearing in the photograph are as true as possible with color illustrations of this type.

In the following description, color references are made to the Royal Horticultural Society color chart (RHS), except where general color terms of ordinary significance are used.

Botanical classification: *Saintpaulia ionantha,* Ramat. cv Alberta.

Parentage:

*Male parent.*—86/75 white star.

*Female parent.*—Velu/Wifo blue.

Propagation: The new cultivar holds its distinguishing characteristics through successive propagations by leaf cuttings and by division of shoots.

Plant: From 10 cm. to 12 cm. tall when grown in pots, and approximately 25–35 cm. in diameter when fully grown. Environmental conditions such as light, etc. obviously affect the growth attained.

Leaves:

*General form.*—Oval.

*Diameter.*—60–65 mm.

*Texture.*—Leather-like.

*Aspect.*—*Slightly hairy.*

*Venis.*—Visible from upperside, well pronounced from underside and hairy.

*Color (upperside).*—RHS 147A.

*Color (underside).*—RHS 148C.

*Petiole.*—Strong; small flat groove on upperside; slightly hairy.

Flowers:

*Buds.*—Bell-shaped; 5–7 cm. in diameter, RHS 78B-C.

*Sepals.*—Color: yellow-green 152 A RHS. Calyx: funnel-shaped. Aspect: spear-shaped. Peduncle: brown-reddish, hairy.

Individual flowers:

*Size.*—30 mm in diameter, flat.

*Color.*—Upperside: center and edges, RHS 78A; other areas white ranging to purple. Underside: White to RHS 77C-D.

*Borne.*—Flower stems carry up to 12 single flowers a few of which show an additional small petal joined at the receptacle. Seed capsule is pushed slightly through.

*Shape.*—Violet-shaped, 2 small petals, 3 large.

*Corolla.*—Main color is white, center and edges are purple.

*Arrangement.*—Flowers are on slightly bent, strong stems, medium green to brown in color and slightly hairy.

*Flowering time.*—6–7 weeks after potting, the first flowers appear; 8–10 weeks to full bloom, with up to 10 flower stems.

Reproductive organs:

*Stamens.*—Two in number.

*Anthers.*—4 cells, color 8A RHS.

*Filaments.*—Slightly bent, yellow-green with partly brown-purple stripes.

*Styles.*—6–8 mm. long, color RHS 78A.

*Pollen color.*—RHS 18C.

Roots: Normally developed; young roots are white, when older turning brownish.

Disease resistance: No disease noticed to date.

General observations: Alberta is a vigorous growing variety with up to 12 and more peduncles, and 12 or more single flowers on each peduncle. The principal color is white, with the center and edges of the flowers being purple. A few flowers have additional petals appearing out of the center of the flower, and the flowers are non-dropping.

I claim:

1. A new and distinct cultivar of African violet, as shown and described, known by the cultivar name Alberta, and characterized by the combined features of vigorous growth habit; producing 12 or more strong flower stems each of which carries 12 or more violet-shaped flowers which are generally white with purple centers and edges, with the flowers normally containing five petals, with an occasional small petal appearing at the center attached to the receptacle; uniform bouquet and by its long blooming period.

* * * * *

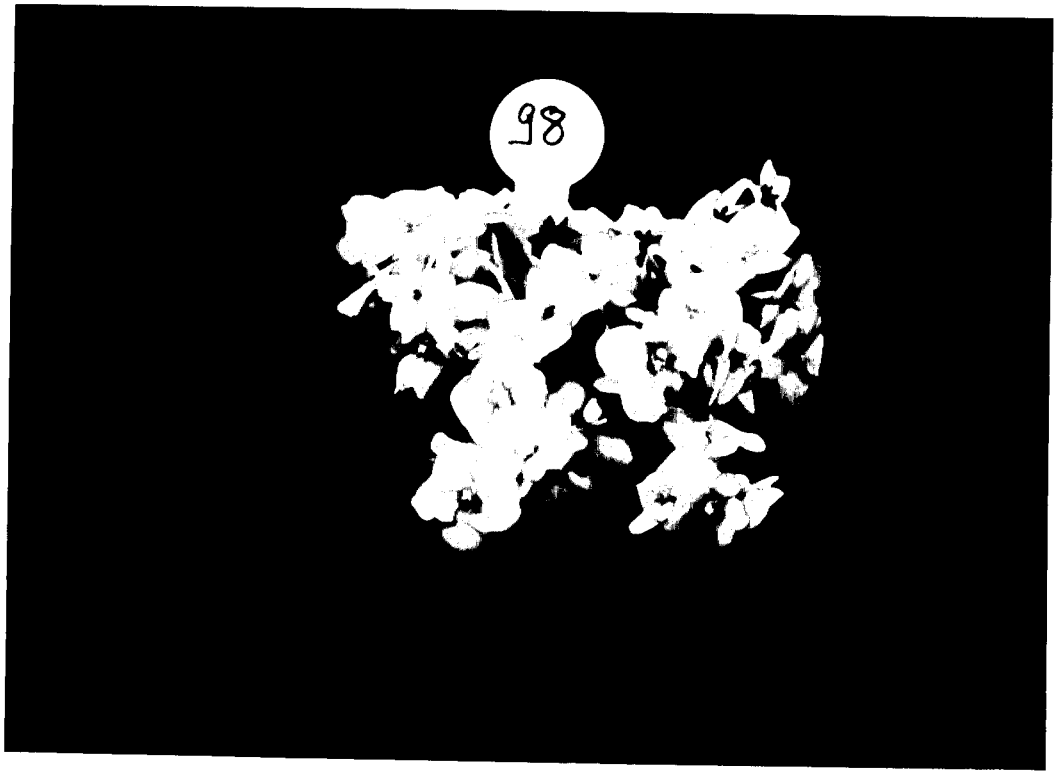
98